(12) United States Patent
Gibson

(10) Patent No.: US 8,774,929 B2
(45) Date of Patent: Jul. 8, 2014

(54) COCHLEAR IMPLANT COMPONENT HAVING A UNITARY FACEPLATE

(75) Inventor: Peter Gibson, South Coogee (AU)

(73) Assignee: Cochlear Limited, Macquarie University, NSW (AU)

( * ) Notice: Subject to any disclaimer, the term of this patent is extended or adjusted under 35 U.S.C. 154(b) by 0 days.

(21) Appl. No.: 13/176,349

(22) Filed: Jul. 5, 2011

(65) Prior Publication Data

US 2011/0264170 A1  Oct. 27, 2011

Related U.S. Application Data

(62) Division of application No. 10/523,795, filed as application No. PCT/AU03/01012 on Aug. 11, 2003, now Pat. No. 7,974,700.

(60) Provisional application No. 60/590,916, filed on Jul. 26, 2004, provisional application No. 60/629,578, filed on Nov. 22, 2004.

(30) Foreign Application Priority Data

Aug. 9, 2002 (AU) ................................. 2002950754

(51) Int. Cl.
*A61N 1/05* (2006.01)
(52) U.S. Cl.
USPC ............... 607/55; 607/36; 607/137; 607/116; 607/57
(58) Field of Classification Search
USPC ................................. 607/36–37, 137, 139, 55
See application file for complete search history.

(56) References Cited

U.S. PATENT DOCUMENTS

| | | | |
|---|---|---|---|
| 2,487,038 A | 11/1949 | Baum | |
| 2,641,328 A | 6/1953 | Beaudry | |
| 3,768,977 A | * 10/1973 | Brumfield et al. | ............. 422/46 |
| 4,055,233 A | 10/1977 | Huntress | |
| 4,333,469 A | 6/1982 | Jeffcoat et al. | |
| 4,488,561 A | 12/1984 | Doring | |
| 4,532,930 A | 8/1985 | Crosby et al. | |
| 4,612,915 A | 9/1986 | Hough et al. | |
| 4,744,792 A | 5/1988 | Sander et al. | |
| 4,904,233 A | 2/1990 | Hankansson et al. | |
| 4,986,831 A | 1/1991 | King et al. | |
| 5,176,620 A | 1/1993 | Gilman | |

(Continued)

FOREIGN PATENT DOCUMENTS

RU  2 282 426 C1  8/2008
WO  83/00999 A1  3/1983

(Continued)

OTHER PUBLICATIONS

International Application No. PCT/AU03/01004, International Preliminary Examination Report mailed on Nov. 22, 2004, 3 Pages.

(Continued)

*Primary Examiner* — Joseph Stoklosa
(74) *Attorney, Agent, or Firm* — K&L Gates, LLP

(57) ABSTRACT

A protective faceplate (37) for an implantable component of a tissue-stimulating prosthesis, such as a prosthetic hearing implant. The faceplate (37) comprising a first or outer surface and an opposed second or inner surface. The implantable component can be removably or non-removably mountable to the second surface and adapted to extend into a cavity formed in a bone of a recipient.

23 Claims, 6 Drawing Sheets

(56) References Cited

U.S. PATENT DOCUMENTS

| | | |
|---|---|---|
| 5,277,694 A | 1/1994 | Leysieffer et al. |
| 5,282,253 A | 1/1994 | Konomi |
| 5,443,493 A | 8/1995 | Byers et al. |
| 5,558,618 A | 9/1996 | Maniglia |
| 5,572,594 A | 11/1996 | Devoe et al. |
| 5,738,521 A | 4/1998 | Dugot |
| 5,814,095 A | 9/1998 | Muller et al. |
| 5,881,158 A | 3/1999 | Lesinski et al. |
| 5,906,635 A | 5/1999 | Maniglia |
| 5,999,632 A | 12/1999 | Leysieffer et al. |
| 6,042,380 A | 3/2000 | De Rowe |
| 6,070,105 A | 5/2000 | Kuzma |
| 6,125,302 A | 9/2000 | Kuzma |
| 6,132,384 A | 10/2000 | Christopherson et al. |
| 6,381,336 B1 * | 4/2002 | Lesinski et al. ............ 381/326 |
| 6,427,086 B1 * | 7/2002 | Fischell et al. ............. 607/45 |
| 6,516,228 B1 | 2/2003 | Berrang et al. |
| 6,537,200 B2 | 3/2003 | Leysieffer et al. |
| 6,565,503 B2 | 5/2003 | Leysieffer et al. |
| 6,575,894 B2 | 6/2003 | Leysieffer et al. |
| 6,697,674 B2 | 2/2004 | Leysieffer |
| 6,730,015 B2 | 5/2004 | Schugt et al. |
| 6,840,919 B1 | 1/2005 | Håkansson |
| 7,043,040 B2 | 5/2006 | Westerkull |
| 7,974,700 B1 | 7/2011 | Gibson |
| 2002/0019669 A1 | 2/2002 | Berrang et al. |
| 2004/0260361 A1 | 12/2004 | Gibson |
| 2006/0116743 A1 | 6/2006 | Gibson et al. |
| 2009/0099658 A1 | 4/2009 | Dalton et al. |
| 2011/0160855 A1 | 6/2011 | Gibson |

FOREIGN PATENT DOCUMENTS

| | | |
|---|---|---|
| WO | 94/29932 A1 | 12/1994 |
| WO | 97/05673 A1 | 2/1997 |
| WO | 97/36457 A1 | 10/1997 |
| WO | 99/06108 A1 | 2/1999 |
| WO | 01/10369 A1 | 2/2001 |
| WO | 03/070133 A1 | 8/2003 |
| WO | 03/092326 A1 | 11/2003 |
| WO | 2004/014269 A1 | 2/2004 |
| WO | 2004/014270 A1 | 2/2004 |
| WO | 2007/053882 A1 | 5/2007 |
| WO | 2009/099658 A2 | 8/2009 |

OTHER PUBLICATIONS

International Application No. PCT/AU03/01004, International Search Report mailed on Oct. 13, 2003, 2 Pages.
International Application No. PCT/AU03/01004, Written Opinion mailed on Sep. 9, 2006, 3 Pages.
International Application No. PCT/AU06/001632, International Preliminary Report on Patentability mailed on May 14, 2008, 6 Pages.
International Application No. PCT/AU06/001632, International Search Report mailed on Dec. 1, 2006, 3 Pages.
International Application No. PCT/AU06/001632, Written Opinion mailed on Dec. 1, 2006, 5 Pages.
International Application No. PCT/AU2000/000936, International Preliminary Examination Report mailed on Jun. 8, 2001, 3 Pages.
International Application No. PCT/AU2003/000229, International Preliminary Examination Report mailed on May 24, 2004, 6 Pages.
International Application No. PCT/AU2003/000229, International Search Report mailed on May 5, 2003, 5 Pages.
International Application No. PCT/AU2003/000229, Written Opinion mailed on Jun. 30, 2003, 6 Pages.
International Application No. PCT/AU2003/001012, International Preliminary Examination Report mailed on Nov. 23, 2004, 3 Pages.
International Application No. PCT/AU2003/001012, International Search Report mailed on Oct. 13, 2005, 5 Pages.
International Application No. PCT/AU2003/001012, Written Opinion mailed on Feb. 23, 2004, 3 Pages.

* cited by examiner

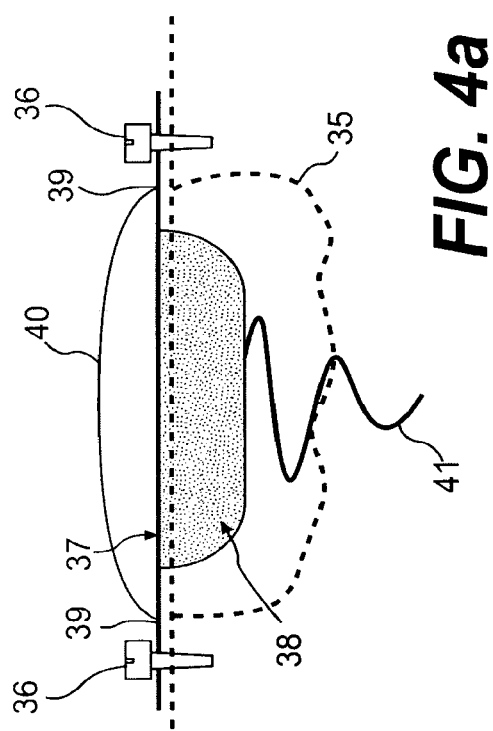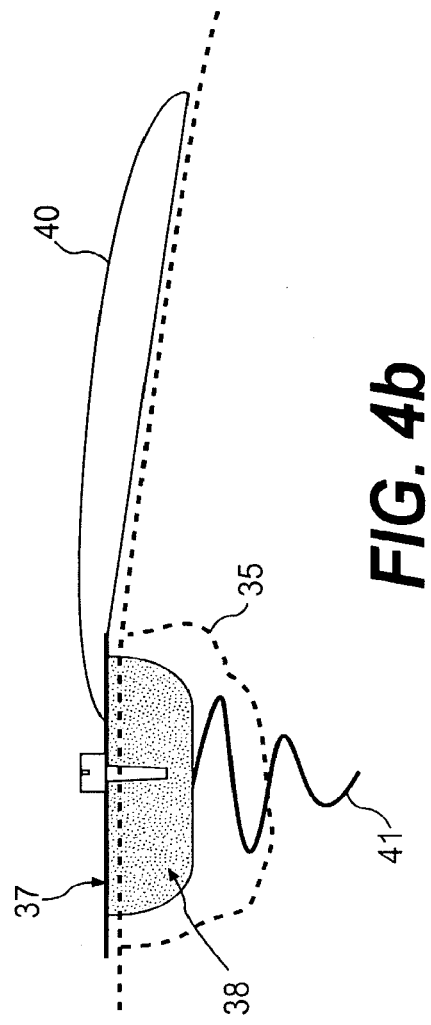

COCHLEAR IMPLANT COMPONENT HAVING A UNITARY FACEPLATE

CROSS-REFERENCE TO RELATED APPLICATION(S)

This application is a divisional application of U.S. patent application Ser. No. 10/523,795 filed on Jun. 30, 2005, which is a national stage application of PCT/AU2003/01012, filed on Aug. 11, 2003, which claims the priority of Australian Patent Application No. 2002950754, filed on Aug. 9, 2002. In addition, this application claims the priority and makes reference to U.S. Provisional Application No. 60/590,916, filed on Jul. 26, 2004, and U.S. Provisional Application No. 60/629,578, filed on Nov. 22, 2004. The entire disclosure and contents of the above patents and applications are hereby incorporated by reference. The present application is also related to U.S. application Ser. No. 10/523,800, entitled "Fixation System for an Implantable Medical Device," filed Feb. 9, 2005.

BACKGROUND

1. Field of the Invention

The present invention resides in an improved method of mounting an implantable component of an implantable medical device, such as a prosthetic hearing implant package, securely in the head region of a recipient.

2. Related Art

In many people who are profoundly deaf, the reason for deafness is absence of, or destruction of, the hair cells in the cochlea which transduce acoustic signals into nerve impulses. These people are unable to derive suitable benefit from conventional hearing aid systems, no matter how loud the acoustic stimulus is made, because there is damage to or absence of the mechanism for nerve impulses to be generated from sound in the normal manner.

It is for this purpose that prosthetic hearing implant systems have been developed. Such systems bypass the hair cells in the cochlea and directly deliver electrical stimulation to the auditory nerve fibres, thereby allowing the brain to perceive a hearing sensation resembling the natural hearing sensation normally delivered to the auditory nerve.

Prosthetic hearing implant systems have typically consisted of essentially two components, an external component commonly referred to as a processor unit and an internal implanted component commonly referred to as a receiver/stimulator unit. Traditionally, both of these components have cooperated together to provide the sound sensation to a user.

The external component has traditionally consisted of a microphone for detecting sounds, such as speech and environmental sounds, a speech processor that converts the detected sounds, particularly speech, into a coded signal, a power source such as a battery, and an external transmitter antenna coil.

The coded signal output by the speech processor is transmitted transcutaneously to the implanted receiver/stimulator unit situated within a recess of the temporal bone of the user. This transcutaneous transmission occurs via the external transmitter antenna which is positioned to communicate with an implanted receiver antenna coil provided with the receiver/stimulator unit.

This communication serves two essential purposes, firstly to transcutaneously transmit the coded sound signal and secondly to provide power to the implanted receiver/stimulator unit. Conventionally, this link has been in the form of a radio frequency (RF) link, but other such links have been proposed and implemented with varying degrees of success.

The implanted receiver/stimulator unit traditionally includes a receiver antenna coil that receives the coded signal and power from the external processor component, and a stimulator that processes the coded signal and outputs a stimulation signal to an intracochlear electrode assembly which applies the electrical stimulation directly to the auditory nerve producing a hearing sensation corresponding to the original detected sound.

As mentioned above, traditional implanted receiver/stimulator units are positioned within the head of the recipient by drilling a bed into and through the posterior section of the mastoid bone lying behind the recipient's ear. Such a bed is usually made by drilling the bone down to the lining of the brain or dura mater, so that the receiver/stimulator unit is securely held in position and does not protrude excessively past the skull surface.

The receiver/stimulator unit manufactured by the present Applicant has a package made from titanium which houses the stimulation electronics and which is fitted into a bed created in the mastoid bone. A receiver antenna coil extends from the rear end of the package and lies superficial to the bone. Other prosthetic hearing implants have included packages made from a ceramic material which are usually placed completely within the bed drilled down to the lining of the brain.

Over time it has been realized that the placing of the above packages in the mastoid bone some distance behind the ear has not always been ideal and has had some problems associated therewith. In instances where young children have been implanted with a device, it has been seen that in some recipients the package has created an external protuberance in the region of the head adjacent the implant site, which has been unsightly, intrusive, and inconvenient for the recipient. In some instances, such a protuberance can prevent the placement of a behind-the-ear processor unit over the site of the implant due to the risk of skin erosion that may result.

Further, as the package is positioned to be facing the surface of the skull, the implant package may be subject to an impact to the head in that region either directly on top of the device or as a lateral glancing blow to the device. In this regard, such devices must be designed to withstand such an impact and remain operational. In this regard, it has been found that by designing the device to have a low profile, the risk of the device sustaining a glancing, lateral blow is less likely. It is also important that the device is designed in such a manner to ensure that it is prevented from entering the cranial cavity in the event of the device being subject to an impact of excessive force.

International PCT Application No. PCT/AU00/00936 discloses an implant package capable of being located within the mastoid cavity of a recipient. This application introduces the utilization of the naturally occurring gutter lying between the sigmoid sinus, posterior osseous ear canal, the mastoid tip and the floor of the middle fossa to protect and maintain the implant package in place. This application discloses a suitably shaped implant casing capable of fitting wholly within the mastoid cavity, having a receiver coil connected thereto via flexible arms. Such a package design may have problems associated with stability of the implant within this cavity region, which could be greatly dependant upon the anatomy of the patient and the particular surgical approach used by the surgeon. Should the package be not firmly secured within the cavity, the implant may move following implantation causing tissue erosion and/or movement of the attached electrode arrays, possibly resulting in the need for re-implantation of the device.

Therefore, there is a need to provide a prosthetic hearing implant package that is capable of addressing at least some of the concerns with prior art devices.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

SUMMARY

According to one aspect of the present invention, a faceplate for protecting an implantable component is provided. The faceplate having dimensions slightly larger than the dimensions of the implantable component securely positioned within a cavity formed in a bone, the faceplate being capable of resting securely on the bone so as to substantially cover the cavity. The faceplate comprises a planar member having an upper and lower surface; and at least one flange extending outwardly beyond the perimeter of the implantable component.

According to another aspect of the present invention, a method of using a faceplate to protect an implantable component secured within a cavity formed in a bone, the implantable component having an upper and lower surface is provided. The method comprises the steps of forming a cavity in a bone of a recipient with dimensions such that the implantable component is capable of being positioned securely within the cavity; positioning the implant in the cavity such that the upper surface is at least in substantial alignment with at least a portion of the surface of the bone surrounding the cavity; and positioning the faceplate to rest securely on the bone, the faceplate having dimensions slightly larger than the dimensions of the implantable component.

According to another aspect of the present invention, a method of using a faceplate to protect an implantable component secured within in a cavity formed in a bone is provided. The method comprises the steps of: forming a cavity in a bone of the recipient with dimensions such that the implantable component is capable of being positioned securely within the cavity; selecting a faceplate having a planar member having an upper and lower surface, the faceplate having a dimensions slightly larger than the dimensions of the implantable component; and positioning the faceplate with the implantable component mounted thereto over the cavity, the faceplate being capable of resting securely on the bone so as to substantially cover the cavity.

BRIEF DESCRIPTION OF THE DRAWINGS

By way of example only, a preferred embodiment of the invention is now described with reference to the accompanying drawings, in which:

FIG. 4a is an end view of the unit and faceplate of FIG. 3 depicted implanted in the mastoid of a recipient;

FIG. 4b is a side view of the unit and faceplate arrangement of FIG. 3;

DETAILED DESCRIPTION

Figure 1:
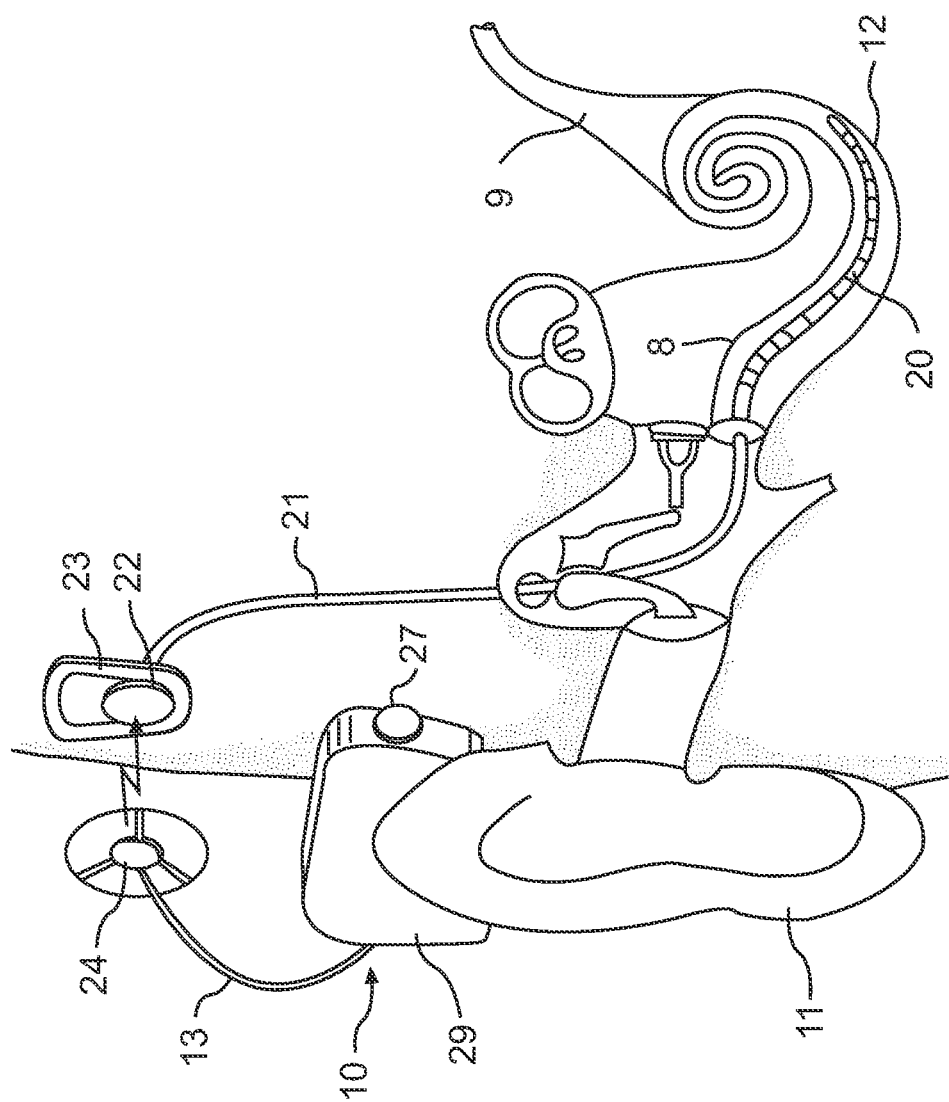
FIG. 1 is a pictorial representation of a conventional prosthetic hearing implant system.

Before describing the features of the present invention, it is appropriate to briefly describe the construction of one type of known prosthetic hearing implant system with reference to FIG. 1.

Known prosthetic hearing implants typically consist of two main components, an external component including a speech processor 29, and an internal component including an implanted receiver and stimulator package 22. The external component includes a microphone 27. The speech processor 29 is, in this illustration, constructed and arranged so that it can fit behind the outer ear 11 and is held in place behind the outer ear 11 via an ear-hook arrangement (not shown). Alternative versions may be worn on the body. Attached to the speech processor 29 via a cable 13 is a transmitter antenna coil 24 that transmits electrical signals to the implanted package 22 via a radio frequency (RF) link.

The implanted component includes a receiver antenna coil 23 for receiving power and data from the transmitter coil 24. A cable 21 extends from the implanted receiver and stimulator package 22 to the cochlea 12 and terminates in an electrode array 20. The signals thus received are applied by the array 20 to the basilar membrane 8 and the nerve cells within the cochlea 12 thereby stimulating the auditory nerve 9. The operation of such a device is described, for example, in U.S. Pat. No. 4,532,930, the contents of which is incorporated herein by reference.

Figure 2:
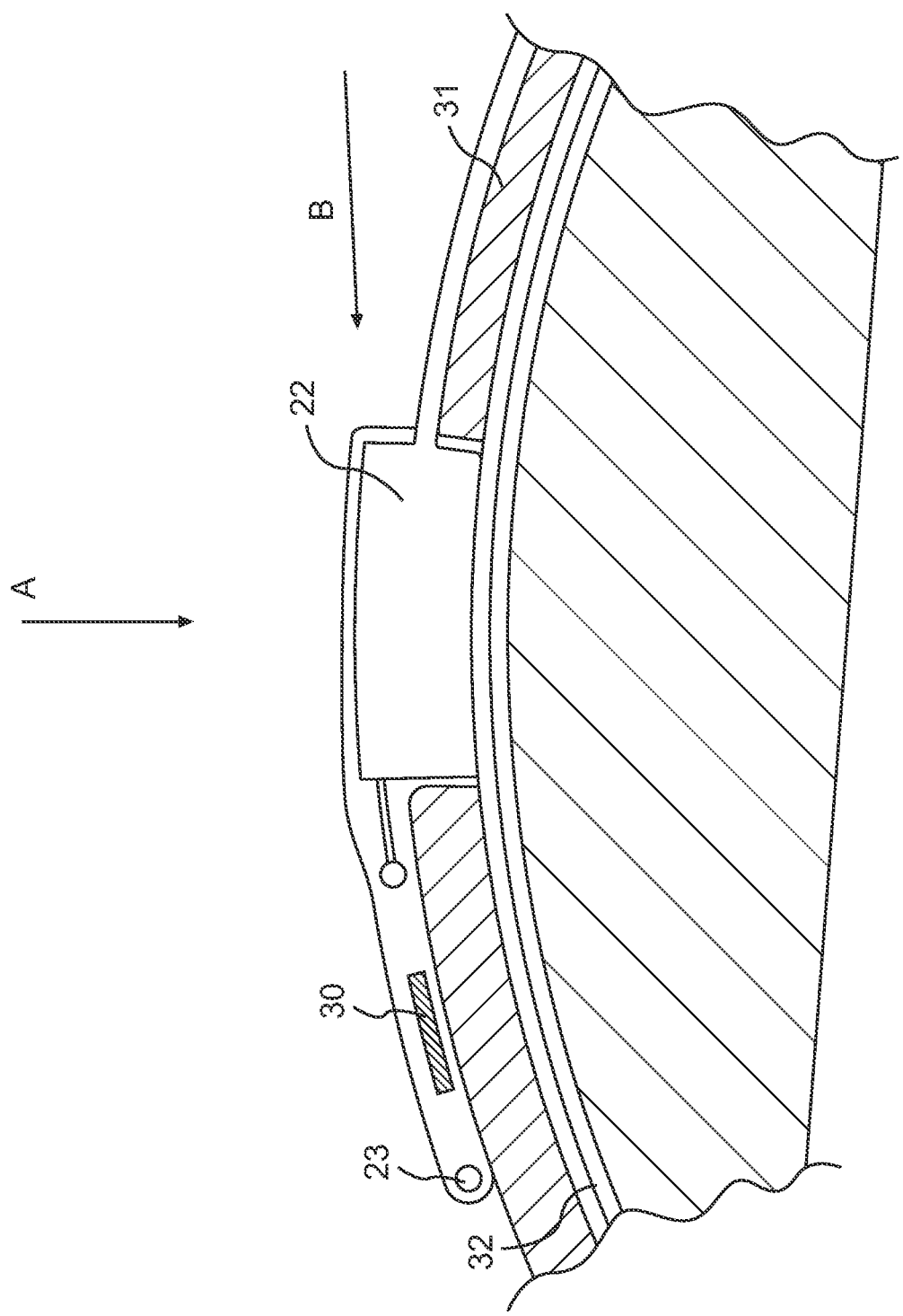
FIG. 2 is a representation of a conventional receiver/stimulator unit positioned in a bed fashioned in the mastoid bone according to conventional surgical techniques.

FIG. 2 shows in more detail the surgical placement of the implanted receiver and stimulator package 22 of FIG. 1, according to conventional practices. The package 22 is in the form of a capsule, for example a titanium capsule, which houses the necessary circuitry required for the implant to operate as desired. The receiver coil 23 is shown encapsulated in a material, such as silicone rubber, to provide a protective body and ensure fatigue resilience. A magnet 30 is shown positioned within the coil to assist in the alignment of the transmitter antenna coil 24 with the receiver antenna coil 23 as discussed previously. As is shown, a bed is drilled into the bone 31 to maintain the package 22 in position. This bed is typically round or ovoid to match the shape of the package. The bed is typically made in the mastoid bone and mastoid angle of the parietal bone in the region of the asterion. Typically, the bed is fashioned initially with a cutting burr, and then completed with a diamond paste burr and a template is typically used to ensure that the bed is fashioned to the correct size. As is shown, the bed may be drilled down to the lining of the brain, or dura mater 32, particularly for young children with thin skulls. It is for this reason that a diamond paste burr may be used when approaching the dura and when the dura is exposed, to minimise the risk of tearing of the dura 32.

As can be seen from FIG. 2, once the receiver and stimulator package 22 is secured in place in the mastoid bone, it remains rather unprotected, with only a layer of skin (not depicted) covering the skull protecting the package from any direct impact. Further to this, it can be appreciated that any impact in the direction shown by the arrow A of FIG. 2, has the potential for the package to tear the dura 32 and enter the cranial cavity, potentially causing damage to the sensitive structures of the brain. As can also be appreciated from FIG. 2, an impact to the head region of the recipient, particularly in the direction shown by arrow B, has the potential to dislodge the implant from its bed within the skull bone. Such dislodgement can cause damage to the area of the head adjacent the device as well as discomfort to the recipient. Any dislodgment of the device also has the potential to require further surgical procedures to relocate the device in the desired position within the head of the recipient.

The present invention aims to address the above potential problems by positioning the receiver/stimulator package in the head in a manner whereby the package preferably has a low profile and its contents are afforded some protection from impact and from being subsequently damaged and/or dislodged.

During a typical surgical procedure for implanting a conventional cochlear prosthetic hearing device, such as this shown in FIGS. 1 and 2, a mastoidectomy and posterior tympanotomy are typically employed to obtain access to the middle ear. The mastoidectomy procedure typically requires removal of material from the mastoid bone behind the ear of the patient via a cutting burr or drill. Typically, the cortex of the mastoid superior and posterior to the external meatus is removed and the excavation is deepened and air cells are removed superior and posterior to the meatus, exposing the mastoid antrum and the middle ear via the tympanotomy. Following the tympanotomy, the round window should be accessible, thereby allowing a cochleostomy to be performed and the electrode array inserted.

It can be understood that by performing a mastoidectomy, a cavity is created which could thereby house the receiver/stimulator package at a location remote from the exterior wall of the skull. It is considered that by allowing the mastoid cavity to house the implant package, considerable advantages can be obtained in relation to the protection and safety of positioning the implant package and the other advantages as discussed previously.

As discussed previously and disclosed in International PCT Patent Application PCT/AU00/00936, anatomical dissections have shown that there exists a "gutter" lying between the sigmoid sinus, posterior osseous ear canal, the mastoid tip and the floor of the middle fossa. This gutter can also form an ideal location to place the implantable receiver/stimulator package, in a position not exposed above the surface of the bone and protected by the pinna.

Figure 3:
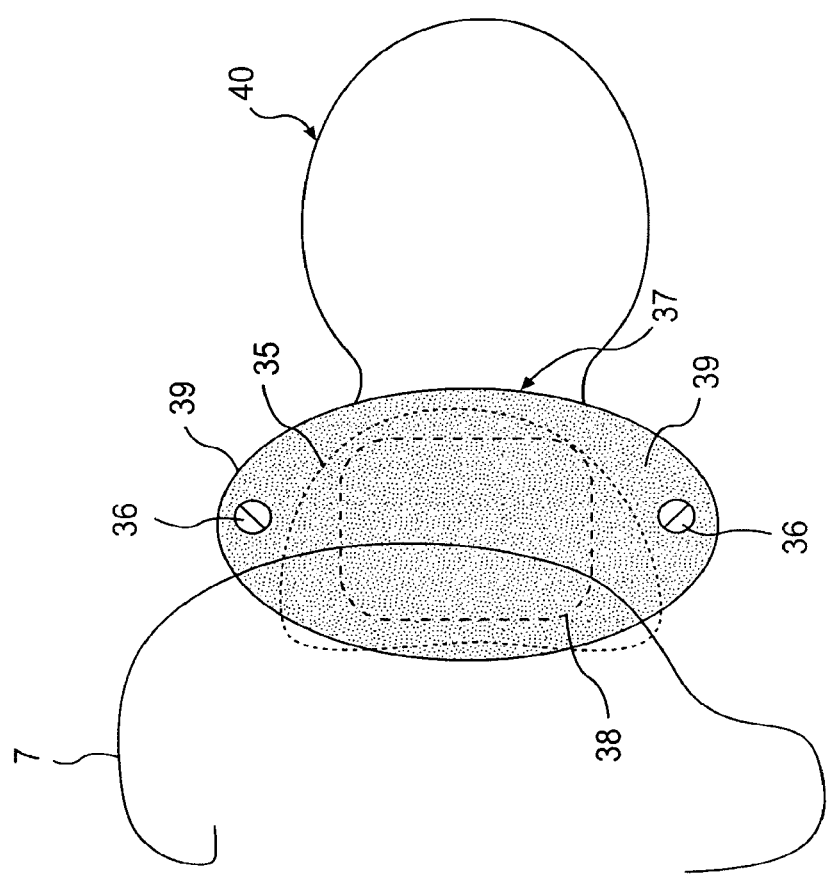
FIG. 3 is a simplified view of the receiver/stimulator unit and faceplate of a prosthetic hearing implant device according to a preferred embodiment of the present invention.

FIG. 3 is a view of one preferred embodiment of the present invention. In this embodiment, the mastoid cavity is shown by the fine dotted line 35, which is shown as being located behind the pinna 11. An upper surface in the form of a top faceplate 37 of the implanted receiver/stimulator unit 38 (heavy dotted line) is shown positioned above and over the mastoid cavity 35. As is evident in FIG. 3, the receiver/stimulator unit 38 has a lower surface that is shaped to be sunk into the mastoid cavity. The depicted faceplate 37 has flanges 39 which extend outside the perimeter of the implanted receiver/stimulator unit 38 to enable securing of the unit to the skull via surgical screws 36. A receiver antenna coil 40 is shown external of the unit 38 and faceplate 37, in much the same manner as a conventional design as discussed previously.

FIGS. 4a and 4b show end and side views of the embodiment depicted in FIG. 3 and where appropriate, the same reference numerals are used. As can be clearly seen in these figures, the receiver/stimulator unit 38 extends into the mastoid cavity 35 and is protected by the faceplate 37 which acts as a protecting shield for the unit 38 as well as a stabiliser and means for securing the unit 38 in place. A lead 41 connects the receiver/stimulator unit 38 to the intracochlear electrodes (not shown) which deliver the electrical stimulation to the nerves within the cochlea.

The flanges of the faceplate 37 can be a simple extension of the upper surface of the receiver/stimulator unit and made from the same material as the rest of the receiver/stimulator unit. This material can, for example, be titanium, preferably a malleable titanium. Alternatively, a titanium flange may be attached to the titanium case of the receiver/stimulator unit 38 by an appropriate welding or other method.

The flanges 39 are formed so as to be relatively robust whilst also sufficiently malleable so that the entire faceplate 37 can be formed to the shape of the skull surrounding the mastoid cavity by the surgeon using finger pressure only. As the anatomy of this region of the head varies somewhat from individual to individual, it is desirable to form the flanges 39 so that they adopt a flush fit in abutment against the skull.

As the faceplate 37 provides protection for the receiver/stimulator unit 38, it is advantageous to form the faceplate from one of a number of different thicknesses of titanium sheet. In order to withstand impacts of considerable force it is desirable to form the faceplate 37 out of a suitable material such as titanium having a thickness of between 0.3 to 1 mm. As the flanges 39 must be malleable to enable a surgeon to alter their shape with a minimum of force, the flanges 39 are, in the depicted embodiment, made from a thinner material than that of the faceplate 37. Alternatively, the desired conformability of the flanges 39 could be achieved by altering their geometry rather than their thickness. In this regard, the flanges 39 could be of the same thickness as the faceplate 37, provided that the flanges are in a narrower strip form rather than a wide flange form. However, in a preferred embodiment, the flanges 39 may be formed from a material, such as titanium, having a thickness of, for example, 0.1 to 0.2 mm.

The lead 41 is preferably pre-coiled so that it can settle into the mastoid cavity 35, below the receiver/stimulator unit 38. As is shown in FIGS. 4a and 4b, the lead 41 exits the receiver/stimulator unit 38 from a bottom surface thereof. This facilitates routing of the lead to the cochlea via the posterior tympanotomy, which is at the bottom of the mastoid cavity. However, it is envisaged that the lead exit point and the form can have many other geometries and still remain within the spirit of the invention. For example, the lead 41 may exit from the side of the receiver/stimulator unit and may be straight.

In order to prevent tissue erosion, the faceplate 37, flanges 39 and screws 36 are preferably coated in a silicone rubber or other elastomeric material. In such a case, the screws 36 would be accessed by means of a slit or hole in the silicone above the screw 36.

It should be appreciated that the screws 36 used in the present invention may have a number of design variations to satisfy the design requirements of the present application. For example, the screws 36 may be countersunk for low profile, may have a round head, and may even be resorbable screws. Resorbable screws would assist in holding the implant in place for a short period until the fibrous tissue surrounds and secures the device in place.

Figure 5:
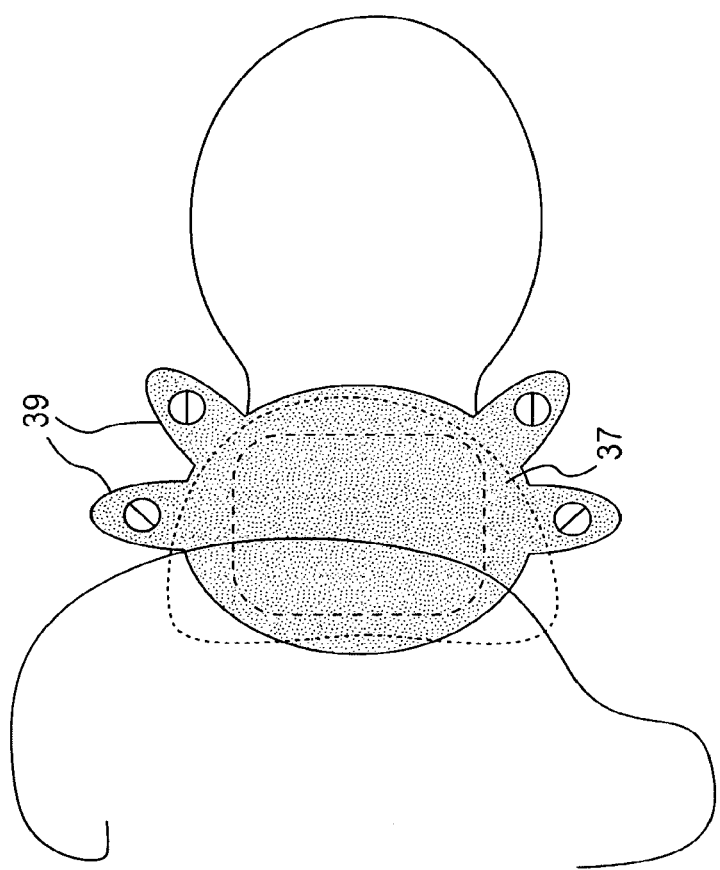
FIG. 5 is a simplified view of another embodiment of a faceplate and receiver/stimulator unit according to the present invention.

FIG. 5 depicts an alternative embodiment of the present invention. In this embodiment, the faceplate has relatively narrow flanges 39 that are adapted to assist in enabling the faceplate 37 to conform to the contours of the skull. Further to this, extra screw holes are provided to allow some redundancy in the variations in patient anatomy and the mastoidectomy performed. Also, if there is a problem with securing the device at one screw site, such as a cavity from a past surgery or a skull growth line, then that screw may be omitted and an alternative screw site used. It should be stressed that this aspect of the present invention is important particularly as it is recommended against fixing the device with screws on both sides of the natural growth lines of the skull. In this embodiment, the basic size of the faceplate 37 is designed to be just larger than the size of the mastoid cavity 35, allowing the faceplate 37 to be stabilised on the rim of the mastoidectomy. To assist in this stabilisation, the rim of the mastoid cavity may be easily flattened by the surgeon, for example by drilling, to create a stable seat for the faceplate 37.

Figure 6:
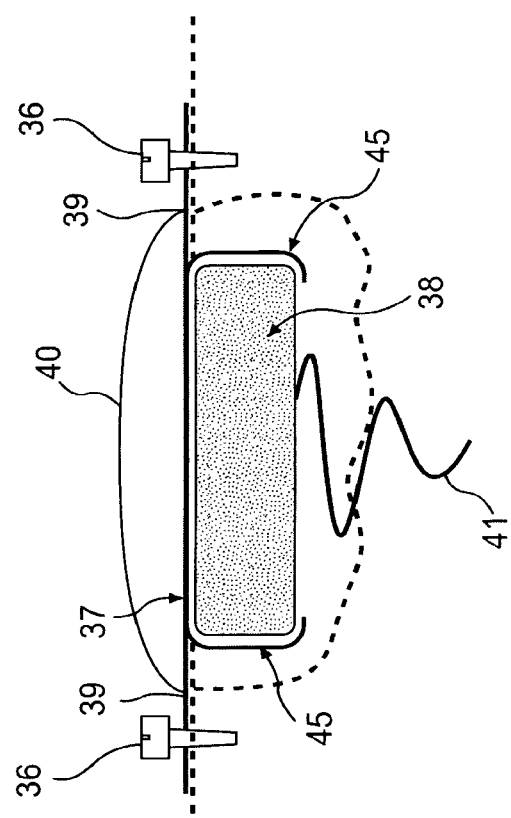
FIG. 6 is an end view of yet another embodiment of a receiver/stimulator unit and faceplate of a prosthetic hearing implant device according to the present invention.

FIG. 6 depicts yet another embodiment of the present invention. In this embodiment, the faceplate and flanges are not fixedly attached to the receiver/stimulator unit 38. The primary difference between this embodiment and that described in FIGS. 4a and 4b is that the faceplate 37 is provided with mechanical catches or clips 45 to hold and maintain the receiver/stimulator unit 38 in place. In this manner, the receiver/stimulator unit is 'snap-fit' into the faceplate 37 for securing in place.

The benefit of this embodiment is that the use of the faceplate and flanges to secure the implant in place is optional and can be decided upon at the time of surgery. Further, the securing mechanism can be used with non-metallic receiver/stimulator units as there is no need for the faceplate and flanges to be welded onto the unit casing. This enables the present device and method to be employed with ceramic cased implants. It is also envisaged that with a detachable system as shown in FIG. 6, the faceplate/flange combination could be made from a non-metallic material such as a biocompatible plastic, as welding to the implant case would not be required. Such a feature would avoid the need to coat the surface of the faceplate and flanges with a coating of silicone rubber and the like to prevent tissue erosion. For example, the plate could be made of polypropylene or polytetrafluoroethylene (PTFE) which have the properties suitable for such an application.

In each of the above-described embodiments of the present invention, the receiver/stimulator unit 38 is shown as an arbitrarily shaped unit capable of fitting within the bone cavity. It is considered that the receiver/stimulator unit 38 could also be conformable such that the shape of the unit 38 may be altered during the procedure to conform to the specific shape of the bone cavity. In this regard, the unit 38 can be made of a conformable material that allows the shape and form of the unit to be changed without effecting the hermiticity of the unit 38.

In each of the above-described embodiments, the procedure associated with implanting a device according to the present invention could generally be as follows:
1. A mastoidectomy would be performed in the same manner as a conventional procedure;
2. Device placement would be determined using a template shaped like the actual implant device;
3. Drill holes would be marked for securing the device in place following the insertion of the electrode array;
4. A posterior tympanotomy and cochleostomy would be performed in the same manner as a conventional procedure;
5. The electrode array would be inserted into the cochlea;
6. The implant package would be placed in position. In this step, the coil connecting the package to the electrode array inserted into the cochlea would preferably coil itself up into the mastoid cavity due to the preformed coil in the lead; and
7. The implant package would be secured in place via screws or the like.

In this manner, the process for implanting a device of the present invention would in no way complicate a conventional procedure and would eliminate the need to drill an additional bed in the mastoid bone for receiving the implant.

While various embodiments of the present invention have been described above, it should be understood that they have been presented by way of example only, and not limitation. It will be apparent to persons skilled in the relevant art that various changes in form and detail may be made therein without departing from the scope of the invention. Thus, the breadth and scope of the present invention should not be limited by any of the above-described exemplary embodiments, but should be defined only in accordance with the following claims and their equivalents.

What is claimed is:

1. A faceplate for protecting an implantable component, the faceplate having dimensions larger than the dimensions of the implantable component securely positioned within a cavity formed in a bone, the faceplate being capable of resting securely on the bone so as to substantially cover the cavity, the faceplate comprising:
   a planar upper and lower surface; and
   at least one flange extending outwardly beyond the perimeter of the implantable component.

2. The faceplate of claim 1, further comprising one or more securing members extending from the lower surface of the faceplate.

3. The faceplate of claim 2, wherein the one or more securing members are configured to removeably mount the implantable component to the faceplate.

4. The faceplate of claim 3, wherein the one or more securing members comprise one or more clips configured to hold the implantable component to the faceplate.

5. The faceplate of claim 1, wherein the at least one flange is securable to the surface of the bone surrounding the cavity.

6. The faceplate of claim 1, wherein the faceplate has two outwardly extending flanges, and wherein the flanges extend in opposite directions relative to each other.

7. The faceplate of claim 1, wherein the at least one flange has a thickness that is greater than the thickness of the portion of the faceplate covering the implantable component.

8. The faceplate of claim 1, wherein the at least one flange has approximately the same thickness as the portion of the faceplate covering the implantable component.

9. The faceplate of claim 1, wherein the at least one flange has at least one orifice extending therethrough that is configured to receive a bone fixation device.

10. The faceplate of claim 9, wherein the bone fixation device is one or more of a bone screw, a bone clip and a bone nail.

11. The faceplate of claim 1, wherein the faceplate is non-metallic.

12. The faceplate of claim 1, wherein the faceplate at least partially comprises a biocompatible plastic.

13. The faceplate of claim 1, wherein the biocompatible plastic comprises at least one of polypropylene and polytetrafluoroethylene (PTFE).

14. A method of using a faceplate to protect an implantable component secured within in a cavity formed in a bone, the implantable component having an upper and lower surface, the method comprising the steps of:
   forming a cavity in a bone of a recipient with dimensions such that the implantable component is capable of being positioned securely within the cavity;

positioning the implant in the cavity such that the upper surface is at least in substantial alignment with at least a portion of the surface of the bone surrounding the cavity; and positioning the faceplate to rest securely on the bone, the faceplate having dimensions larger than the dimensions of the implantable component.

15. The method of claim 14, wherein the faceplate is formed of a malleable material.

16. The method of claim 14, wherein the faceplate comprises a planar member having an upper and lower surface, and at least one flange extending outwardly beyond the perimeter of the implantable component.

17. The method of claim 16, wherein the faceplate comprises one or more securing members extending from the lower surface of the faceplate.

18. A method of using a faceplate to protect an implantable component secured within a cavity formed in a bone, the method comprising the steps of:

forming a cavity in a bone of the recipient with dimensions such that the implantable component is capable of being positioned securely within the cavity;

selecting a faceplate having a planar member having an upper and lower surface, the faceplate having a dimensions larger than the dimensions of the implantable component; and positioning the faceplate with the implantable component mounted thereto over the cavity, the faceplate being capable of resting securely on the bone so as to substantially cover the cavity.

19. The method of claim 18, wherein the faceplate comprises one or more securing members extending from the lower surface of the faceplate.

20. The method of claim 14, wherein the faceplate completely covers the cavity when positioned to securely rest on the bone.

21. The faceplate of claim 1, wherein:

a body forming the planar upper and lower surface and the at least one flange are part of a monolithic component.

22. The method of claim 14, wherein:

the action of positioning the implant in the cavity is executed without the faceplate attached to the implant.

23. The method of claim 18, further including:

attaching the faceplate to the implantable component in between the actions of selecting the faceplate and positioning the faceplate.

* * * * *